United States Patent [19]

Lorraine et al.

[11] Patent Number: 5,801,312

[45] Date of Patent: Sep. 1, 1998

[54] METHOD AND SYSTEM FOR LASER ULTRASONIC IMAGING OF AN OBJECT

[75] Inventors: Peter William Lorraine, Niskayuna; Ralph Allen Hewes, Burnt Hills; Phillip Randall Staver, Hagaman, all of N.Y.

[73] Assignee: General Electric Company, Schenectady, N.Y.

[21] Appl. No.: 627,670

[22] Filed: Apr. 1, 1996

[51] Int. Cl.[6] .......................... G01N 29/06; G01N 29/10; G01N 29/22

[52] U.S. Cl. .................. 73/602; 73/620; 73/643; 73/655; 73/657; 600/443; 600/444

[58] Field of Search .............. 128/660.02, 660.03, 128/661.01, 660.07, 653.1, 916; 364/413.25; 73/602, 606, 618, 620, 621, 625, 627, 629, 632, 643, 655–657

[56] References Cited

U.S. PATENT DOCUMENTS

| | | | |
|---|---|---|---|
| 3,548,642 | 12/1970 | Flaherty et al. | 73/602 |
| 3,978,713 | 9/1976 | Penney | 73/643 |
| 4,164,740 | 8/1979 | Constant | 342/25 |
| 4,597,292 | 7/1986 | Fujii et al. | 73/599 |
| 4,841,489 | 6/1989 | Ozaki et al. | 73/633 |
| 5,384,573 | 1/1995 | Turpin | 342/179 |
| 5,549,002 | 8/1996 | Howard et al. | 73/602 |
| 5,608,166 | 3/1997 | Monchalin et al. | 73/657 |
| 5,615,675 | 4/1997 | O'Donnell et al. | 128/653.1 |

OTHER PUBLICATIONS

"Imaging Defects With Laser Ultrasound" By DA Hutchins, et al, Nondestructive Testing Communications, vol. 5, No. 2–3, 1990 (UK), pp. 85–96.

"A New System for Real–Time Synthetic Aperture Ultrasonic Imaging" By Y. Ozaki, et al, IEEE Transactions on Ultrasonics, Ferroelectrics, and Frequency Control, vol. 35, No. 6, Nov. 1988, pp. 828–838.

*Primary Examiner*—Hezron E. Williams
*Assistant Examiner*—Rose M. Miller
*Attorney, Agent, or Firm*—David C. Goldman; Marvin Snyder

[57] ABSTRACT

The present invention discloses a method and system for laser ultrasonic imaging an object. In the present invention, a synthetic aperture focusing technique (SAFT) is used to generate a high resolution subsurface images of the object. In addition, the present invention filters low frequency components from detected laser ultrasound waveform data to further enhance resolution, SNR, and contrast. Geometric knowledge permits the present invention to generate images of objects having a complex and arbitrary-shape.

12 Claims, 7 Drawing Sheets

METHOD AND SYSTEM FOR LASER ULTRASONIC IMAGING OF AN OBJECT

BACKGROUND OF THE INVENTION

The present invention relates generally to the nondestructive evaluation of engineering materials, and more particularly to laser ultrasonic imaging of engineering materials using a synthetic aperture focusing technique.

Laser ultrasound involves the generation or detection of ultrasound in materials with lasers. Generally, in laser ultrasonic imaging, a source laser irradiates a material with laser beams along its surface. Ultrasonic waves may be generated by laser beams either by non-destructive local heating of the surface to create expansion and a strain wave (i.e., thermoelastic generation) or by increasing the amplitude of the beams to vaporize a small amount (e.g., <1 micron) of material to form a plasma that strikes the surface like a hammer (i.e., ablation generation). The ultrasonic waves propagate throughout the material and are reflected back to the surface of the material. As the reflected ultrasonic waves return to the surface of the material, an interferometric detector is used to detect either displacement at the surface or ultrasonic wave velocity by simultaneously irradiating the surface with a laser beam. The detected displacement or velocity signals are then used to generate a volumetric image of the material. A more detailed discussion on laser ultrasonics is provided in *Laser Ultrasonics—Techniques and Applications* by C. B. Scruby and L. E. Drain (IOP Publishing Ltd., 1990), which is incorporated herein by reference.

A problem associated with conventional laser ultrasonic imaging techniques is that the generated images have poor resolution. The resolution is poor because the laser detector is unable to focus and therefore identify the exact spatial location of any reflectors within the material which give rise to the detected signals. In addition, the resolution is poor because the laser detector is generally sensitive to the normal component of motion and does not differentiate between different directions of arrival of the reflected ultrasonic wave. For these reasons, current laser ultrasonic imaging techniques have been unable to generate high resolution subsurface images of defects within engineering materials. Attempts to overcome the poor resolution have used patterns of light such as lines, rings, arcs, or discrete beams at multiple locations. Rings and lines focus moderately well on the surface, but do not provide much resolution at depths within the material, and arrays of sources have only modest subsurface directionality due to the limited number of sources available. A further problem with these approaches and the conventional laser ultrasonic imaging approach is that the source laser produces an unipolar ultrasound pulse and does not provide destructive interference at non-image points and results in a broad, raised background around the reflectors. Still another problem associated with these approaches is that it is difficult to obtain high resolution images of complex and arbitrary-shaped materials.

SUMMARY OF THE INVENTION

Therefore, it is a primary objective of the present invention to provide a method and system for generating laser ultrasonic focussed images with high resolution across a surface or throughout a volume of material.

Another object of the present invention is to apply synthetic aperture focusing techniques (SAFT) to detected laser waveform data in order to attain focussed images.

Still another object of the present invention is to filter the detected laser waveform data to remove low frequency components in order to greatly enhance resolution and contrast.

A further object of the present invention is to use geometric knowledge of the material being imaged with the SAFT to generate high resolution images of complex, arbitrary-shaped materials.

Yet another object of the present invention is to use geometric knowledge of the material being imaged with the SAFT to generate high resolution images of objects having as-machined surfaces formed by lathes, milling machines, or the like.

Thus, in accordance with the present invention, there is provided a method and system for laser ultrasonic imaging an object. In the present invention, a surface of the object is scanned with a source laser emitting a laser beam at a plurality of scanning positions along the object surface. The emitted laser beam generates ultrasonic sound waves at the plurality of scanning positions and transmits the ultrasonic sound waves within the object. The surface of the object is also scanned with a detection laser emitting a laser beam at the plurality of scanning positions. Surface displacement produced by ultrasonic sound waves reflected from within the object are detected with an interferometric detector at each scanning position. The detected displacement at each scanning position contain signals representing a laser ultrasonic waveform data set corresponding to a three-dimensional volumetric region in the object. The laser ultrasonic waveform data sets are processed at each scanning position with a synthetic aperture focusing technique wherein the three-dimensional waveform data sets are coherently summed along a time of flight locus curve forming an image of the three-dimensional volumetric region in the object.

While the present invention will hereinafter be described in connection with a preferred embodiment and method of use, it will be understood that it is not intended to limit the invention to this embodiment. Instead, it is intended to cover all alternatives, modifications and equivalents as may be included within the spirit and scope of the present invention as defined by the appended claims.

DETAILED DESCRIPTION OF THE PRESENT INVENTION

Figure 1:
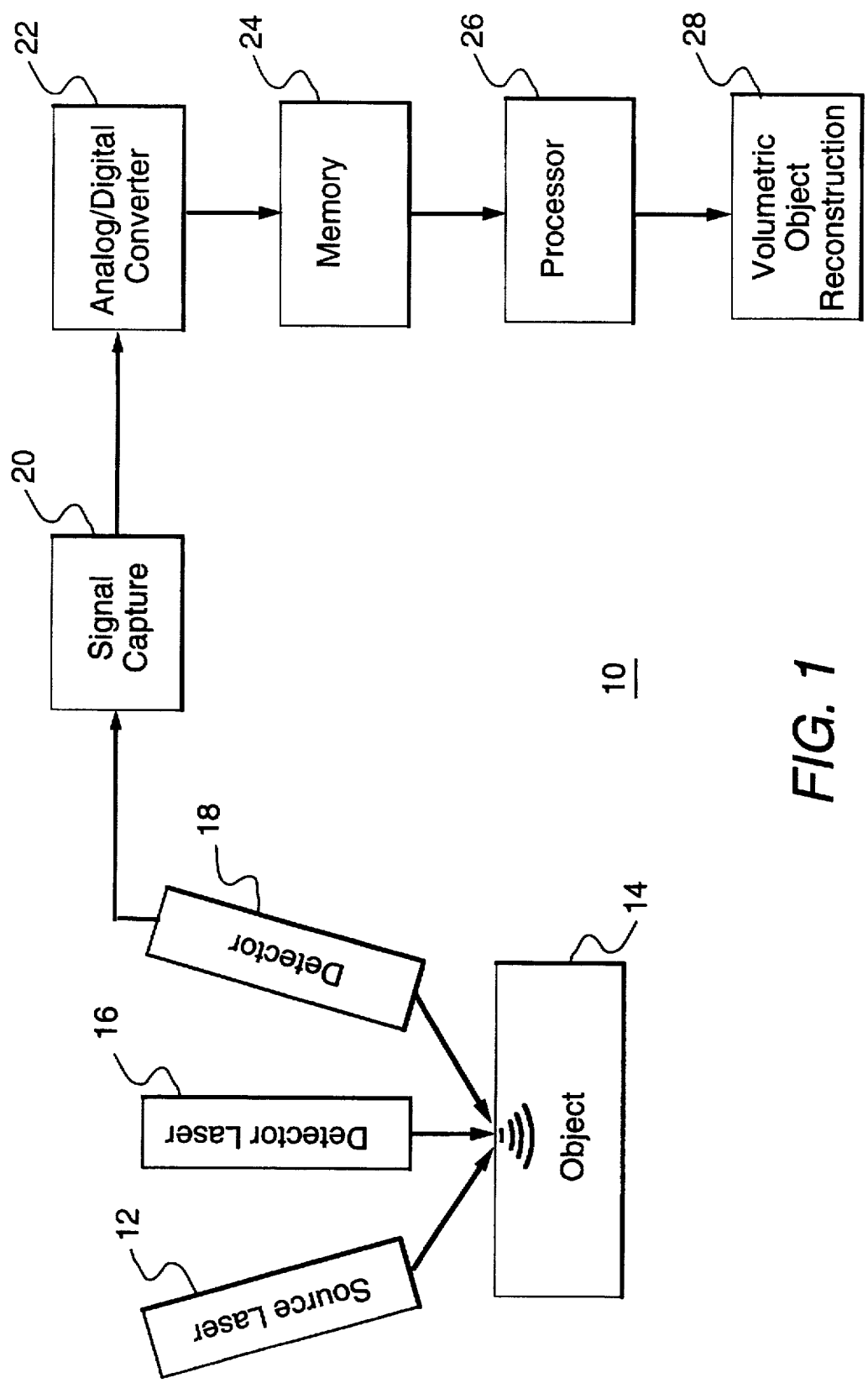
FIG. 1 shows a block diagram of a laser ultrasonic imaging system according to a first embodiment of the present invention.

FIG. 1 shows a block diagram of a laser ultrasonic imaging system 10 used in the present invention. In the laser ultrasonic imaging system 10, a source laser 12 is scanned over the surface of an object 14. The object may be an engineering material such as titanium or a nickel based alloy. The source laser 12 irradiates the object 14 with a laser beam along its surface at a plurality of scanning positions. The laser beam generated from the source laser 12 has a high energy appropriate to the inspection, but generally is less than $5 \times 10^8$ W/cm$^2$. Ultrasonic waves are generated by laser beams either by non-destructive local heating of the surface to create expansion and a strain wave or by increasing the amplitude of the beams to vaporize a small amount (e.g., <1 micron) of material to form a plasma that strikes the surface like a hammer. The laser source spot size will influence the ultrasound beam spread in the object and should be tailored to match the desired aperture size and detection depth. The spot energy may also be adjusted to vary the angular spread of ultrasound energy. In addition, more complex temporal and spatial modulation of the source laser spot may also be incorporated to enhance performance. The generated ultrasonic waves propagate throughout the object 14 and are reflected back to the surface. As the reflected ultrasonic waves return to the surface of the object, a detection laser 16 is used to detect either displacement at the surface or ultrasonic wave velocity by simultaneously irradiating the surface with a laser beam. The laser beam generated from the detection laser 16 has line width, stability, and fluence suitable for interferometric detection. A detector 18, typically a sensitive interferometric detector, detects and amplifies the displacement or velocity signals and outputs the signals to a signal capture 20. The amplified signals represent a laser ultrasonic waveform data set corresponding to a three-dimensional volumetric region within the object 14. These signals are then digitized by an A/D converter 22 and stored in a memory 24. The laser ultrasonic waveform data stored in the memory are processed by a processor 26. The processor using the technique of the present invention, which is described later in further detail, reconstructs a volumetric image of the object that is displayed on a display 28.

Figure 2:
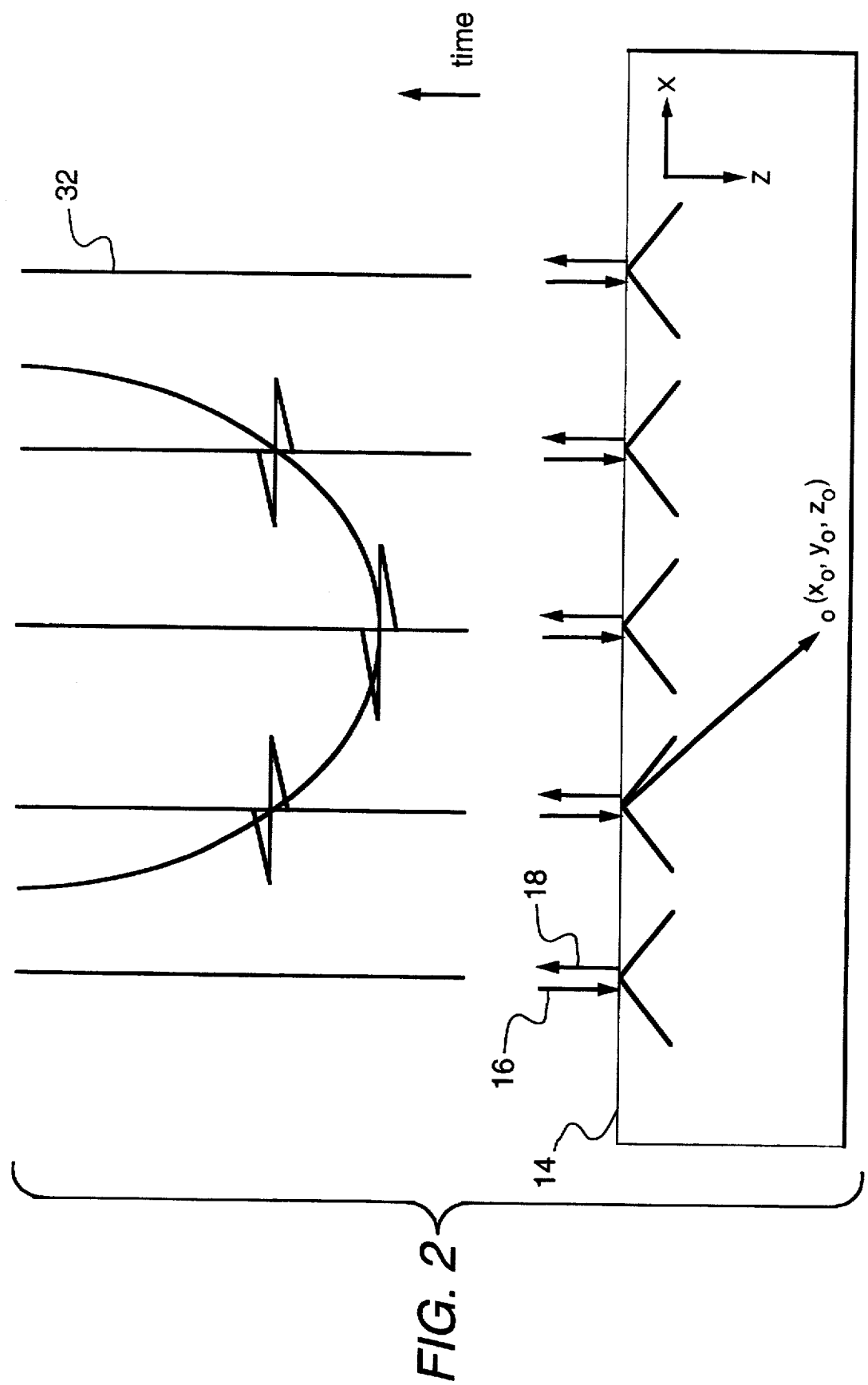
FIG. 2 shows a schematic diagram of image reconstruction with the laser ultrasonic imaging system.

FIG. 2 shows a schematic diagram of image reconstruction for the laser ultrasonic imaging system 10. In FIG. 2, the detector laser 16 and detector 18 is scanned linearly in the x-direction over the surface of object 14. At each spatial position, the detector laser 16 irradiates the surface of the object 14 with a laser beam to detect the displacement of the ultrasonic waves reflected from within the object. In FIG. 2, the reflected ultrasonic waves are caused by reflectors 30 located within the object 14. The detector 18 detects the displacement at the surface of the object at each scanning position. In the present invention, the laser ultrasonic waveform data corresponds to displacement. In the illustrative embodiment, the detector 18 receives a back scattered signal (i.e., an A scan) at a constant spatial interval $\Delta x$ and $\Delta y$. The top portion of FIG. 2 shows the relationship between the detector laser 16 and the detector 18 on the surface of the object and the acoustic reflector $(x_o, y_o, z_o)$ 30 in the part that has a reflectivity $r(x_o, y_o, z_o)$. In particular, the time of flight $t(x)$ between the point of focus of the detector laser 16 and the detector 18 and the acoustic reflector is represented by a hyperbolic curve 32. At the first spatial interval $\Delta x$, the acoustic reflector $(x_o, y_o, z_o)$ is not within the generated ultrasonic sound wave and therefore a back scatter signal is not detected by the detector laser 16 and the detector 18. However, in the next three spatial intervals, the acoustic reflector $(x_o, y_o, z_o)$ is within the generated ultrasonic sound wave and back scatter signals are detected by the detector laser 16 and the detector 18. At the last spatial interval, the acoustic reflector $(x_o, y_o, z_o)$ is again not within the generated ultrasonic sound wave and a back scatter signal is not detected by the detector laser 16 and the detector 18. The image of the acoustic reflector is produced by coherently summing up the detected back scatter signals that are on the hyperbolic curve for all the acoustic reflectors within the object.

As mentioned above, a problem with conventional laser ultrasonic imaging systems is that the source laser produces an unipolar ultrasound pulse and does not provide destructive interference at non-image points, resulting in a broad, raised background around the reflectors 30. The present invention has solved this problem by filtering the low frequency components of the laser ultrasonic waveform data. In the illustrative embodiment, the filtering is performed by the processor 26. However, the filtering may be accomplished by analog electronics such as an RC circuit. Removal of the lower frequency components within the laser ultrasonic waveform data permits generation of high resolution images without the broad background.

Figure 3D:
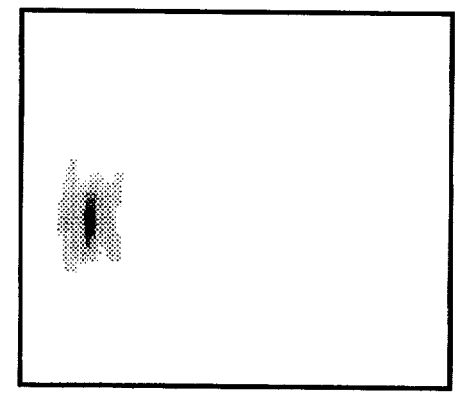
FIGS. 3a–3d show a series of B-scan data generated from the laser ultrasonic imaging system.
Figure 3C:
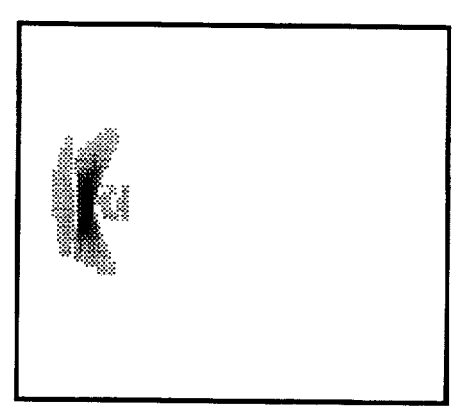
Figure 3B:
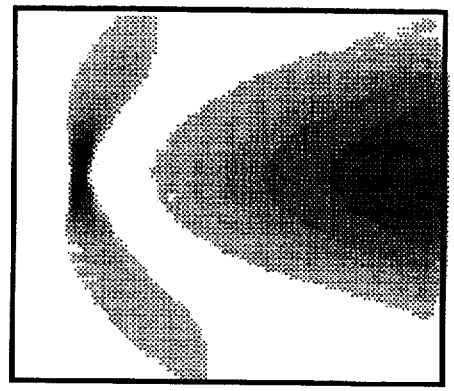
Figure 3A:
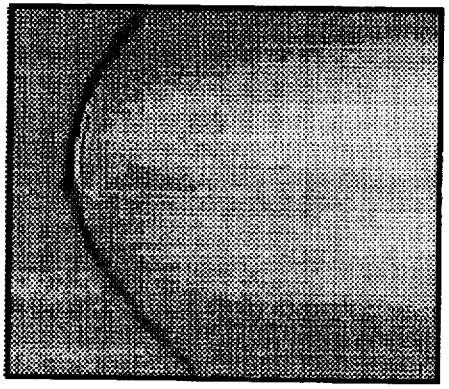

FIGS. 3d a–3d show a series of B-scan data generated from the laser ultrasonic imaging system 10. The B-scan data are images of the laser ultrasonic waveform amplitude as a function of spatial coordinate (i.e., the horizontal axis) and time (i.e., the vertical axis). The raw data in FIG. 3a shows a hyperbolic curve typical of point reflectors generated in a conventional unfocussed laser ultrasonic imaging system. FIG. 3b shows the effect that SAFT has on the raw data. In particular, the SAFT has the immediate effect of localizing the sound source to a specific region of space. If a digitizer samples a waveform at a rate of "X" samples per second, then the Nyquist frequency (i.e., $f_{Nyquist}$), the highest frequency that is present in the data without artifacts, is "X/2". FIG. 3c shows the effect that a high pass filter operating with a cutoff of $f_{Nyquist}/20$ prior to SAFT imaging. FIG. 3d shows the effect that a high pass filter operating with a cutoff of $f_{Nyquist}/10$ prior to SAFT imaging. In particular, the effect of raising the low frequency cutoff will decrease the focal spot size and improve the resolution. As a result, the SAFT processed data generated from the present invention will provide a SNR of about 40 db, whereas the SNR of the raw data generated from the conventional unfocussed laser ultrasonic imaging system is only about 15 dB.

Figure 4D:
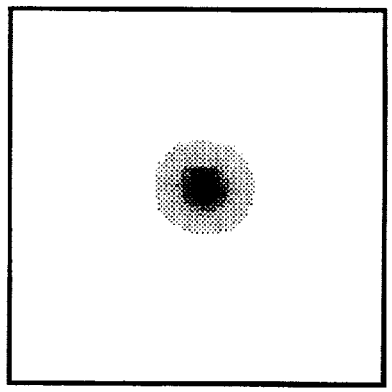
FIGS. 4a–4d show a series of C-scan data generated from the laser ultrasonic imaging system.
Figure 4C:
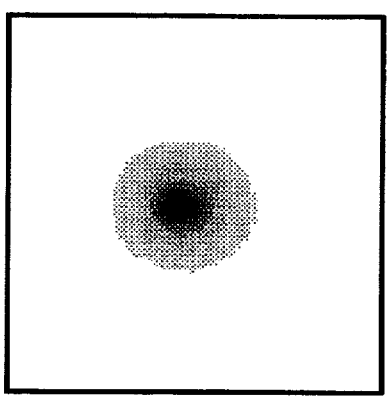
Figure 4B:
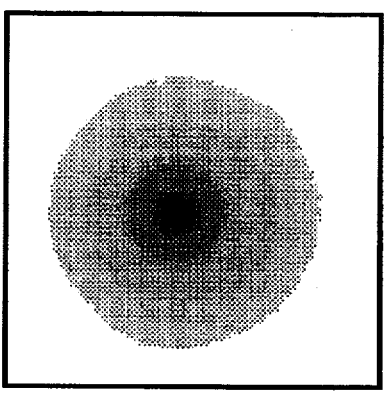
Figure 4A:
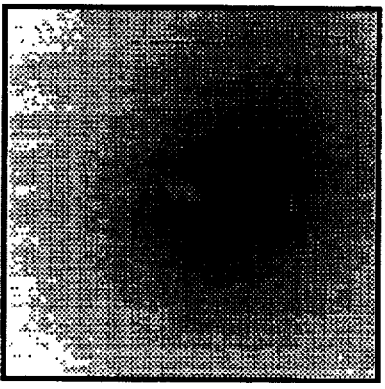

FIGS. 4a–4d show a series of C-scan data generated from the laser ultrasonic imaging system 10. The C-scan data show images at each location, and in particular the maximum intensity in the data set within certain time limits. The raw data in FIG. 4a shows an example of raw data generated in a conventional unfocussed laser ultrasonic imaging system. FIG. 4b shows the effect that SAFT has on the raw data with a high pass filter operating with a cutoff of $f_{Nyquist}/20$. In particular, the SAFT has the immediate effect of localizing the sound source to a specific region of space. FIG. 4c shows the effect that a high pass filter operating with a cutoff of $f_{Nyquist}/20$ prior to SAFT imaging. FIG. 4d shows the effect that a high pass filter operating with a cutoff of $f_{Nyquist}/10$ prior to SAFT imaging.

Figures 5B, 5C:
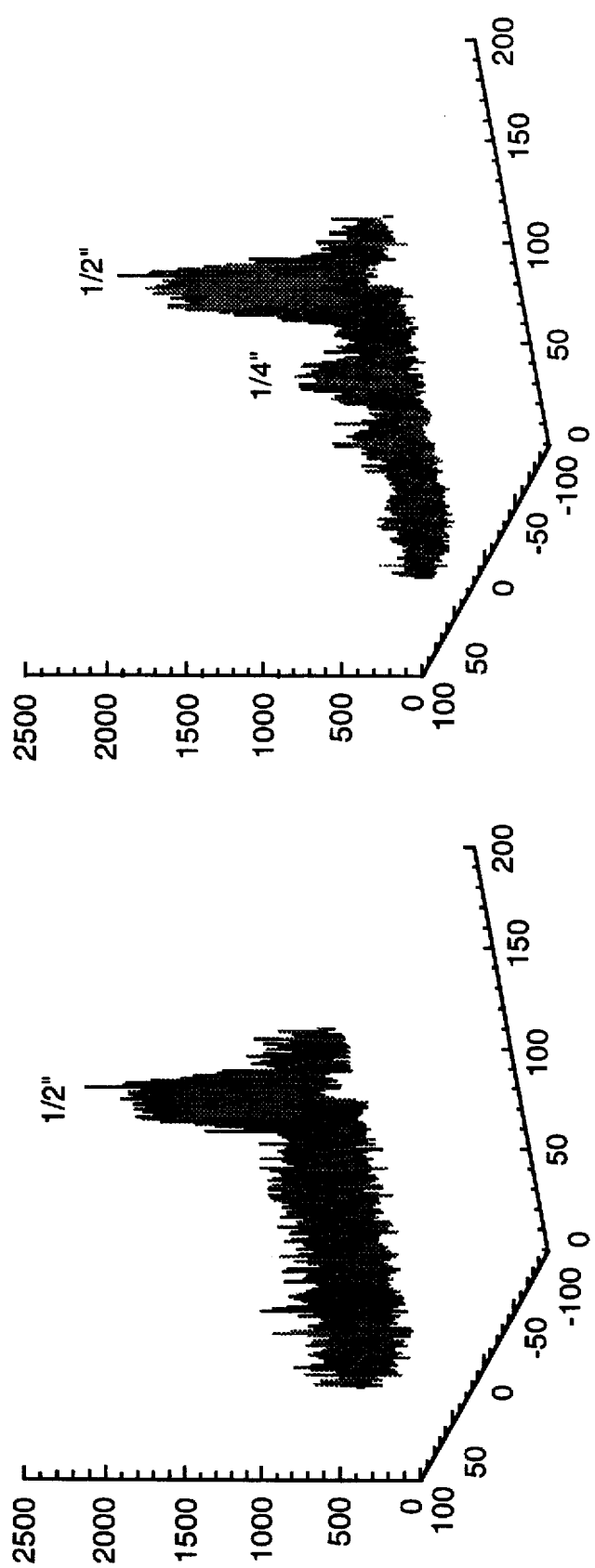
FIGS. 5a–5d shows a series of C-scan data generated from a titanium block having varying holes drilled therein.
Figure 5D:
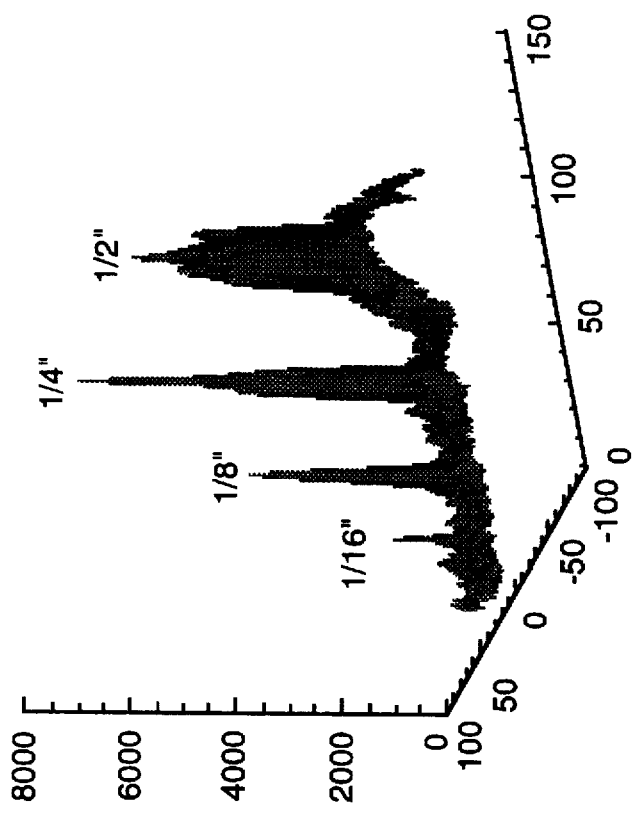
Figure 5A:
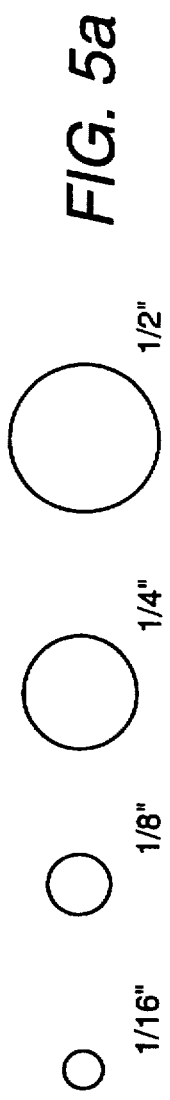

The improvement in image quality that is provided with the present invention is further shown by the series of C-scans in FIGS. 5a–5d. The C-scans were taken from a 2.5" thick titanium 6-4 block having various sizes of flat-bottom holes drilled ½" deep from the back face of the block. FIG. 5a shows the varying sizes of holes (i.e., 1/16 inch, 1/8 inch, ¼ inch, and ½ inch) drilled into the back of the block. FIG. 5b shows an example of raw data generated in a conventional unfocussed laser ultrasonic imaging system. As can be seen, only the largest reflector, from the ½ inch hole is able to be imaged. FIG. 5c shows the effect that filtering has on the raw data. In particular, filtering the data to remove noise barely enables the ¼ inch hole to be seen. FIG. 5d shows the effect that SAFT has on the raw data. In particular, SAFT processing on the raw data reveals all four reflectors from the ¹/₁₆ inch, ⅛ inch, ¼ inch, and ½ inch holes. The SAFT processing clearly enhances the ability to detect small reflectors with laser ultrasound.

In another embodiment of the present invention, the laser ultrasonic imaging with SAFT is used to image complex, arbitrary-shaped geometries. Typically, complex, arbitrary-shaped geometries present a further imaging problem to conventional laser ultrasonic imaging systems. Normally, the conventional laser ultrasonic imaging systems are used to image planar or simple geometries and are unable to image complex, arbitrary-shaped geometries, such as engineering materials manufactured for the aerospace industry (i.e., engine components such as blades, disks, and panels), where it is very important to be able to image these materials for the detection of defects. The present invention has overcome these problems of the conventional laser ultrasonic imaging system by measuring part geometry of the material and using the above-described SAFT reconstruction to obtain images of complex, arbitrary-shaped materials with high resolution and sensitivity. In the present invention, the part geometry may be measured by registering the material with well known techniques such as CAD models, Coordinate Measuring Machines (CMM), or vision-based methods. The geometry knowledge is used by the SAFT reconstruction to calculate a distance to an image point. From an estimate of the material sound velocity, the travel time is then calculated. By incorporating the geometry of the part, the calculated travel times are correct and coherent summation of waveforms occurs.

Figure 6:
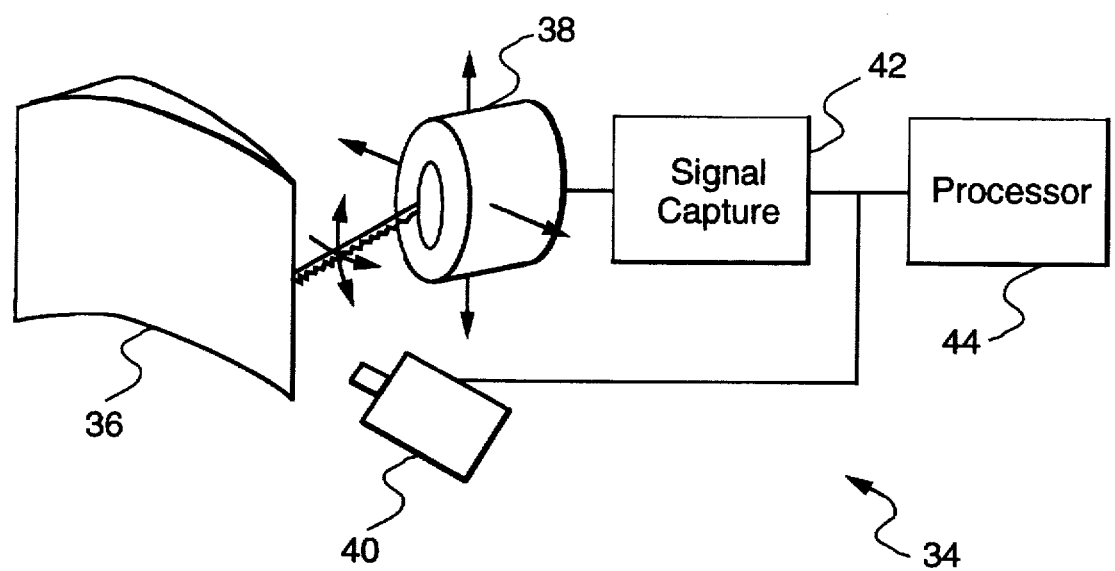
FIG. 6 shows a laser ultrasonic imaging system for imaging a complex, arbitrary shaped object according to a second embodiment of the present invention.

FIG. 6 shows a laser ultrasonic imaging system 34 for imaging a complex, arbitrary shaped object 36. In the laser ultrasonic imaging system 34, a hybrid scan head 38 is scanned over the surface of an object 36. The hybrid scan head 38 irradiates the object 36 with a laser beam along its surface at a plurality of scanning positions. A signal capture means 42 detects and amplifies the signals generated from the hybrid scan head 38. Ultrasonic waves are generated by laser beams either by non-destructive local heating of the surface to create expansion and a strain wave or by increasing the amplitude of the beams to vaporize a small amount (e.g., <1 micron) of material to form a plasma that strikes the surface like a hammer. The generated ultrasonic waves propagate throughout the object 36 and are reflected back to the surface. As the reflected ultrasonic waves return to the surface of the object, a detector laser 40 is used to detect either displacement at the surface or ultrasonic wave velocity by simultaneously irradiating the surface with a laser beam. The detector 40 detects and amplifies the displacement and outputs the signals to a processor 44, where the amplified signals are then digitized and stored in a memory. The laser ultrasonic waveform data stored in the memory are then processed with the SAFT and the part geometry knowledge by the processor 44 and displayed for reconstructing a volumetric image for detecting and characterizing flaws in the object 36.

Figure 7:
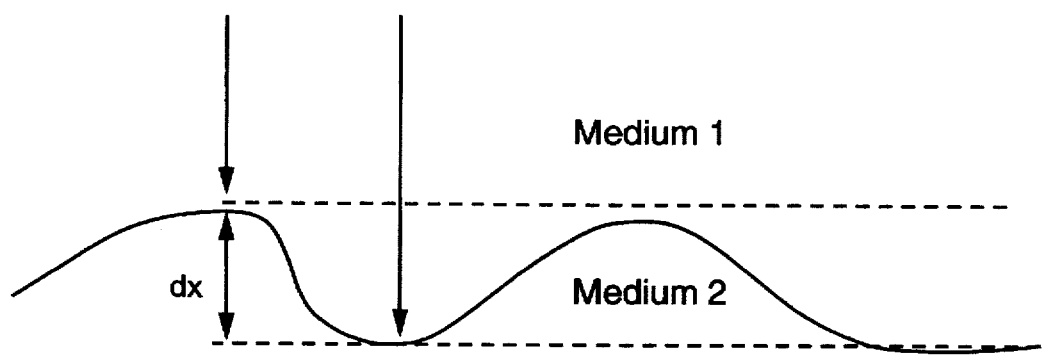
FIG. 7 shows the effect of surface finish on the sensitivity of the laser ultrasonic imaging system according to the second embodiment.

Another problem addressed by the present invention, is the requirement that objects being imaged with a conventional immersion piezoelectric ultrasonic imaging system have a high quality smooth surface. Typically, in a conventional immersion piezoelectric ultrasonic imaging system, the object must have a high quality smooth surface for imaging because a rough surface will degrade performance by introducing random phase variations across the transducer aperture. The laser ultrasonic imaging system 34 obviates the need for applying a high quality smooth surface to objects and can inspect "as-machined" parts formed by lathes, milling machines, or the like. In particular, the effect that the present invention has on the surface roughness may be shown by considering the maximum round trip phase shift of the generated ultrasonic wave after propagation through mediums like water and a metal to a plane below a certain roughness (FIG. 7). The effect is described by equation 1:

$$\Delta \Phi = 4\pi f \frac{v_2 - v_1}{v_1 v_2} dx, \text{ wherein} \tag{1}$$

$v_2$, $v_1$, and $dx$ are the velocity of sound in a second material and a first material having a surface roughness $dx$. For example, in immersion piezoelectric ultrasound inspection of titanium, titanium has a $v_2$ of approximately 6 mm·μsec$^{-1}$ and water has a velocity of sound $v_1$ of approximately 1.5 mm·μsec$^{-1}$. In the present invention, $v_1$ will equal $3 \times 10^5$ mm·μsec$^{-1}$ (the speed of light). For a phase error tolerance of π/3, and a surface roughness of 25 microns, the maximum frequencies that generate images for laser and immersion ultrasound are $f_{LUT}$=20 MHz and $f_{Conv}$=6.6 MHz. In this embodiment, the effect of surface roughness is reduced by a factor of three times for laser ultrasound, resulting in significant cost savings since it is not necessary to provide a high quality surface finish prior to inspection. The advantage of this embodiment is that the laser ultrasonic imaging system is able to rapidly scan arbitrary-shaped objects, to perform longitudinal and/or shear wave imaging by using appropriate software, attain high resolution and SNR volumetric images, permit dynamic control of scan resolution and speed, and acquire phase insensitive images by using applicable software.

It is therefore apparent that there has been provided in accordance with the present invention, a method and system for laser ultrasonic imaging an object that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

The invention claimed is:

1. A method for laser ultrasonic imaging an object, comprising the steps of:

scanning a surface of the object with a source laser emitting a laser beam at a plurality of scanning positions along the object surface, the emitted laser beam generating ultrasonic sound waves at the plurality of scanning positions and transmitting the ultrasonic sound waves within the object;

scanning the surface of the object with a detector laser emitting a laser beam onto the object surface at the plurality of scanning positions;

detecting surface displacement produced by ultrasonic sound waves reflected from within the object with a detector at each scanning position, the detected displacement at each scanning position containing signals representing a laser ultrasound waveform data set corresponding to a three-dimensional volumetric region in the object;

filtering each of the laser ultrasound waveform data sets to restore a bipolar signal suitable for use in a synthetic aperture focusing technique; and processing the laser ultrasound waveform data sets at each scanning position with a synthetic aperture focusing technique wherein the laser ultrasound waveform data sets are coherently summed along a time of flight locus curve forming an image of the three-dimensional volumetric region in the object.

2. The method according to claim 1, further comprising the step of filtering low frequency components from each of the laser ultrasound waveform data sets.

3. The method according to claim 1, further comprising the step of displaying the reconstructed image of the object.

4. The method according to claim 1, wherein the object comprises a complex, arbitrary-shaped material.

5. The method according to claim 4, wherein the step of processing uses geometry knowledge of the complex, arbitrary-shaped object with the synthetic aperture focusing technique to image the object.

6. The method according to claim 5, wherein the complex, arbitrary-shaped object is an as-machine part.

7. A system for laser ultrasonic imaging an object, comprising:

a source laser for scanning a surface of the object, the source laser emitting a first laser beam at a plurality of scanning positions along the object surface, the first emitted laser beam generating ultrasonic sound waves at the plurality of scanning positions and transmitting the ultrasonic sound waves within the object;

a detector laser for scanning the surface of the object, the detector laser emitting a second laser beam onto the object surface at the plurality of scanning positions;

a detector for detecting surface displacement produced by ultrasonic sound waves reflected from within the object, the detected displacement at each scanning position containing signals representing a laser ultrasonic waveform data set corresponding to a three-dimensional volumetric region in the object;

means for filtering each of the laser ultrasonic waveform data sets to restore a bipolar signal suitable for use in a synthetic aperture focusing technique; and means for processing the laser ultrasonic waveform data sets each scanning position with a synthetic aperture focusing technique wherein the laser ultrasonic data sets are coherently summed along a time of flight locus curve forming an image of the three-dimensional volumetric region in the object.

8. The system according to claim 7, further comprising means for filtering low frequency components from each of the laser ultrasonic waveform data sets.

9. The system according to claim 7, further comprising a display for displaying the reconstructed image of the object.

10. The system according to claim 7, wherein the object comprises a complex, arbitrary-shaped material.

11. The system according to claim 10, wherein the processing means uses geometry knowledge of the complex, arbitrary-shaped object with the synthetic aperture focusing technique to image the object.

12. The system according to claim 11, wherein the complex, arbitrary-shaped object is an as-machine part.

* * * * *